(12) United States Patent  
Brady et al.

(10) Patent No.: US 7,789,860 B2
(45) Date of Patent: Sep. 7, 2010

(54) CATHETER FOR DELIVERY AND/OR RETRIEVAL OF A MEDICAL DEVICE

(75) Inventors: Eamon Brady, Elphin (IE); Fergal Farrell, Athy (IE)

(73) Assignee: Salviac Limited, Dublin (IE)

( * ) Notice: Subject to any disclaimer, the term of this patent is extended or adjusted under 35 U.S.C. 154(b) by 1279 days.

(21) Appl. No.: 10/180,971

(22) Filed: Jun. 27, 2002

(65) Prior Publication Data

US 2003/0097095 A1    May 22, 2003

Related U.S. Application Data

(60) Provisional application No. 60/301,820, filed on Jul. 2, 2001.

(30) Foreign Application Priority Data

Jun. 27, 2001    (IE) ................... 2001/0591

(51) Int. Cl.
A61M 5/178 (2006.01)
(52) U.S. Cl. ................................. 604/164.13
(58) Field of Classification Search ............. 604/94.01, 604/264, 273, 524, 160, 161, 164.01–164.09, 604/164.12–164.13, 164.013, 165.01–165.02, 604/284, 535, 103.04
See application file for complete search history.

(56) References Cited

U.S. PATENT DOCUMENTS

| 5,040,548 | A |   | 8/1991  | Yock |
| 5,201,757 | A |   | 4/1993  | Heyn et al. |
| 5,350,395 | A |   | 9/1994  | Yock |
| 5,360,401 | A |   | 11/1994 | Turnland |
| 5,445,646 | A |   | 8/1995  | Euteneuer et al. |
| 5,451,233 | A |   | 9/1995  | Yock |
| 5,527,292 | A | * | 6/1996  | Adams et al. ............... 604/171 |
| 5,534,007 | A |   | 7/1996  | St. Germain et al. |
| 5,690,644 | A | * | 11/1997 | Yurek et al. ................. 623/1.11 |
| 5,738,667 | A |   | 4/1998  | Solar |
| 5,817,101 | A |   | 10/1998 | Fiedler |
| 5,968,052 | A |   | 10/1999 | Sullivan, III et al. |
| 5,993,460 | A |   | 11/1999 | Beitelia et al. |
| 6,042,588 | A |   | 3/2000  | Munsinger et al. |
| 6,113,608 | A |   | 9/2000  | Monroe et al. |
| 6,117,140 | A |   | 9/2000  | Munsinger |
| 6,120,522 | A |   | 9/2000  | Vrba et al. |

(Continued)

FOREIGN PATENT DOCUMENTS

EP    819411 A2    1/1998

(Continued)

*Primary Examiner*—Nicholas D Lucchesi
*Assistant Examiner*—Christopher D Koharski
(74) *Attorney, Agent, or Firm*—Sughrue Mion, PLLC; Jonathan Feuchtwang

(57) ABSTRACT

A catheter for delivery or retrieval of a medical device such as a filter 10 or a stent 16 has an outer shaft 1 with a pod 2 providing a medical device reception space at the distal end. An inner shaft 3 includes a solid pod with a longitudinally extending surface pathway 4 for a guidewire 7. The inner shaft 3 defines an abutment surface 9 at its distal end for deployment of the device 10, 16. The outer shaft 1 has an exit port 8 at which the guidewire 7 exits the catheter in a rapid exchange manner.

60 Claims, 15 Drawing Sheets

U.S. PATENT DOCUMENTS

| | | | |
|---|---|---|---|
| 6,142,987 A * | 11/2000 | Tsugita | 604/500 |
| 6,146,415 A | 11/2000 | Fitz | |
| 6,165,167 A | 12/2000 | Delaloye | |
| 6,165,197 A | 12/2000 | Yock | |
| 6,171,327 B1 | 1/2001 | Daniel et al. | |
| 6,174,327 B1 | 1/2001 | Mertens et al. | |
| 6,228,110 B1 | 5/2001 | Munsinger | |
| 6,238,410 B1 | 5/2001 | Vrba et al. | |
| 6,346,116 B1 | 2/2002 | Brooks et al. | |
| 6,380,457 B1 | 4/2002 | Yurek et al. | |
| 6,488,655 B1 * | 12/2002 | Wantink et al. | 604/103.09 |
| 6,585,719 B2 * | 7/2003 | Wang | 604/525 |
| 6,613,075 B1 * | 9/2003 | Healy et al. | 623/1.11 |
| 2002/0004667 A1 | 1/2002 | Adams et al. | |
| 2002/0029075 A1 | 3/2002 | Leonhardt | |
| 2002/0032461 A1 | 3/2002 | Marshall | |
| 2002/0042626 A1 | 4/2002 | Hanson et al. | |
| 2002/0082525 A1 | 6/2002 | Oslund et al. | |

FOREIGN PATENT DOCUMENTS

| | | |
|---|---|---|
| WO | WO 98/33443 A1 | 8/1998 |
| WO | WO 99/49808 A1 | 10/1999 |
| WO | WO 99/56801 A2 | 11/1999 |
| WO | WO 00/16705 A1 | 3/2000 |
| WO | WO 00/69499 A1 | 11/2000 |
| WO | WO 01/08743 A1 | 2/2001 |
| WO | WO 01/66178 A1 | 9/2001 |
| WO | WO 01/80777 A2 | 11/2001 |

* cited by examiner

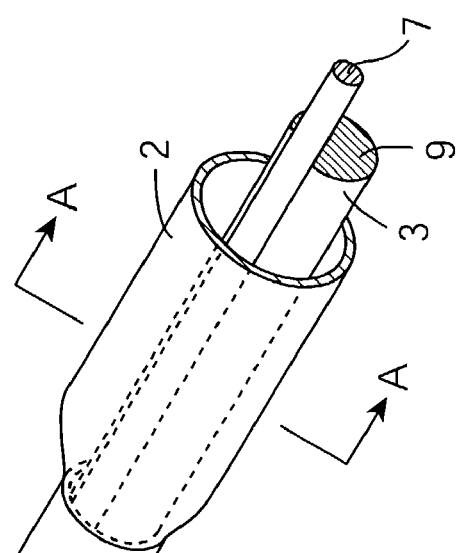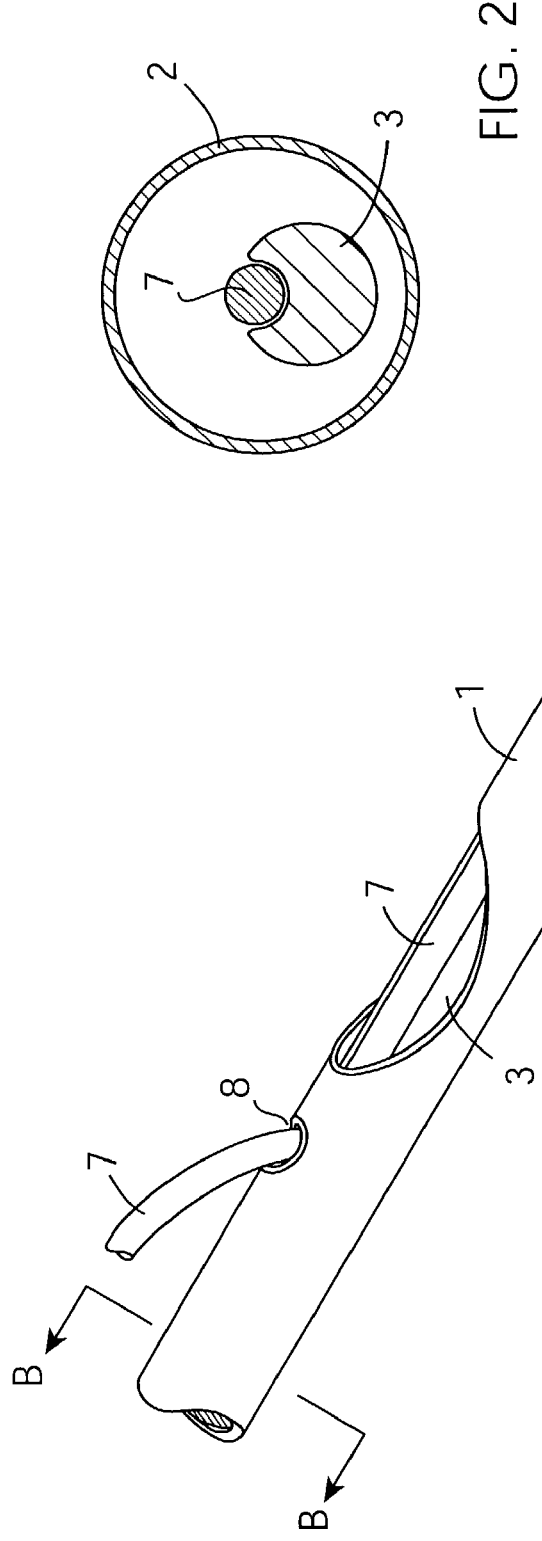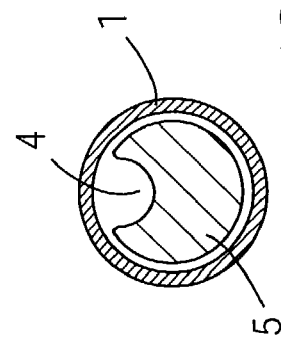

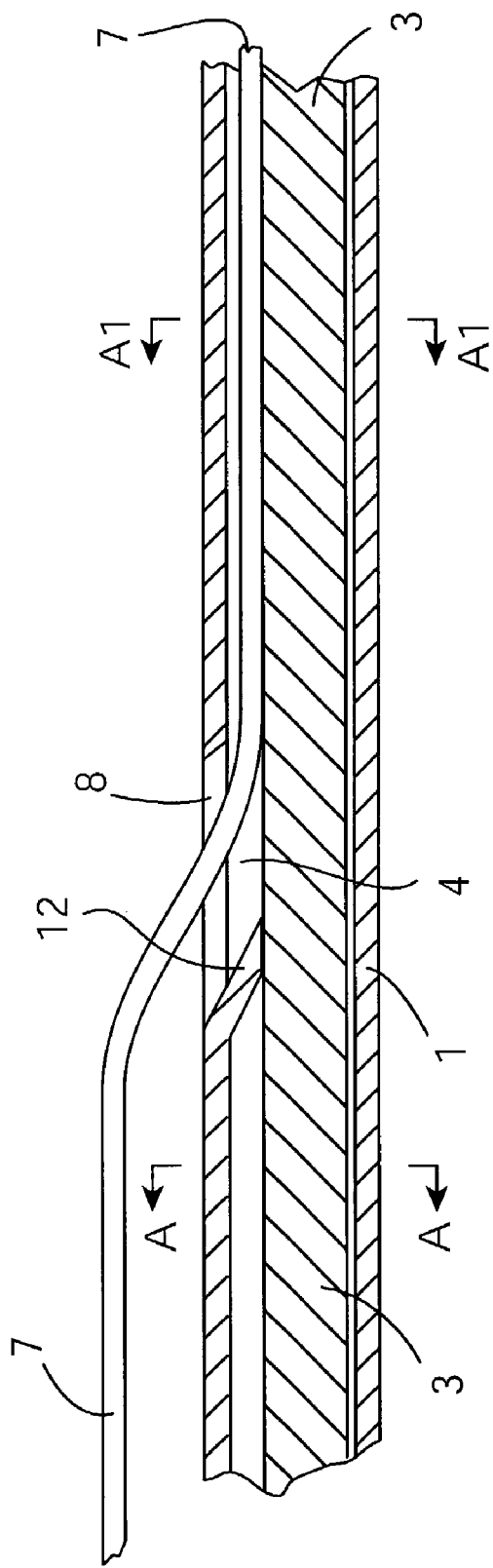
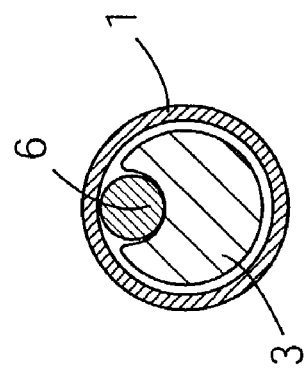
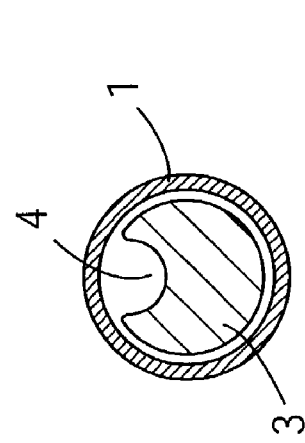

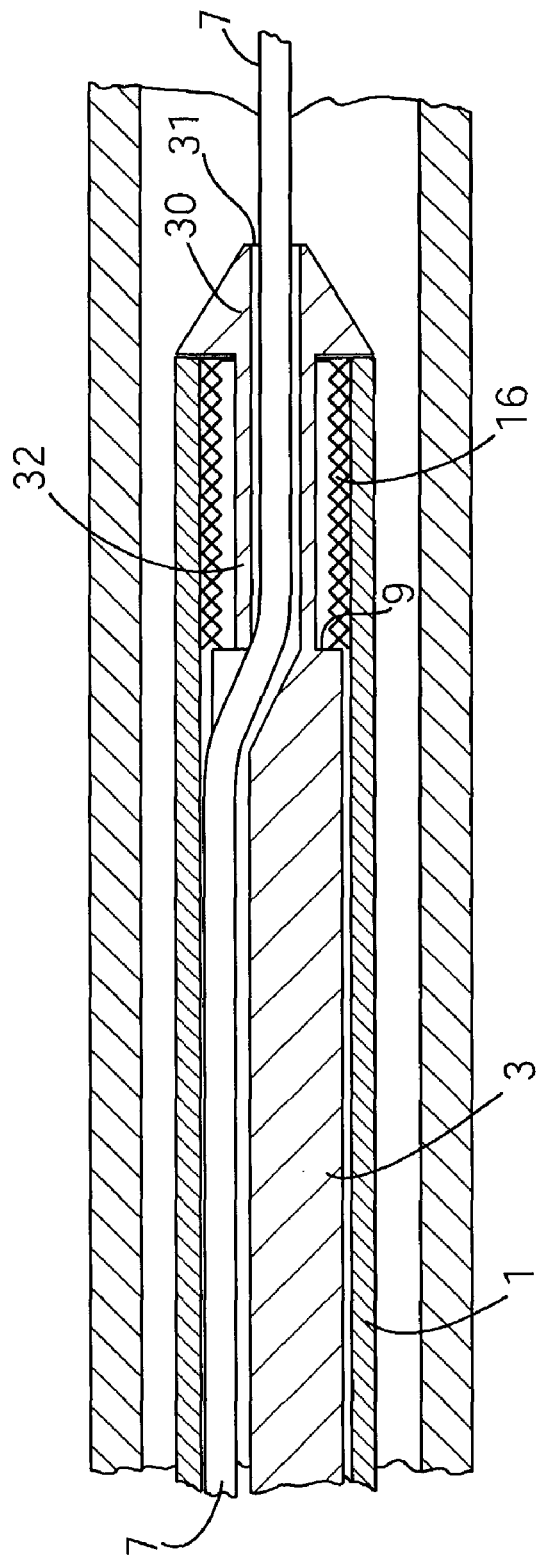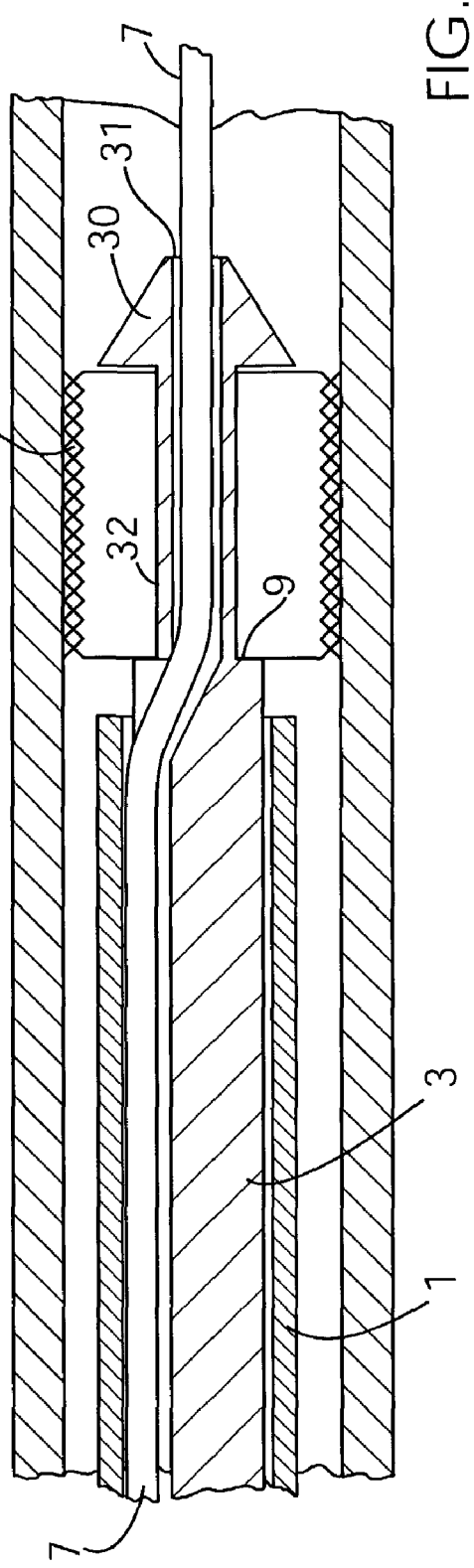

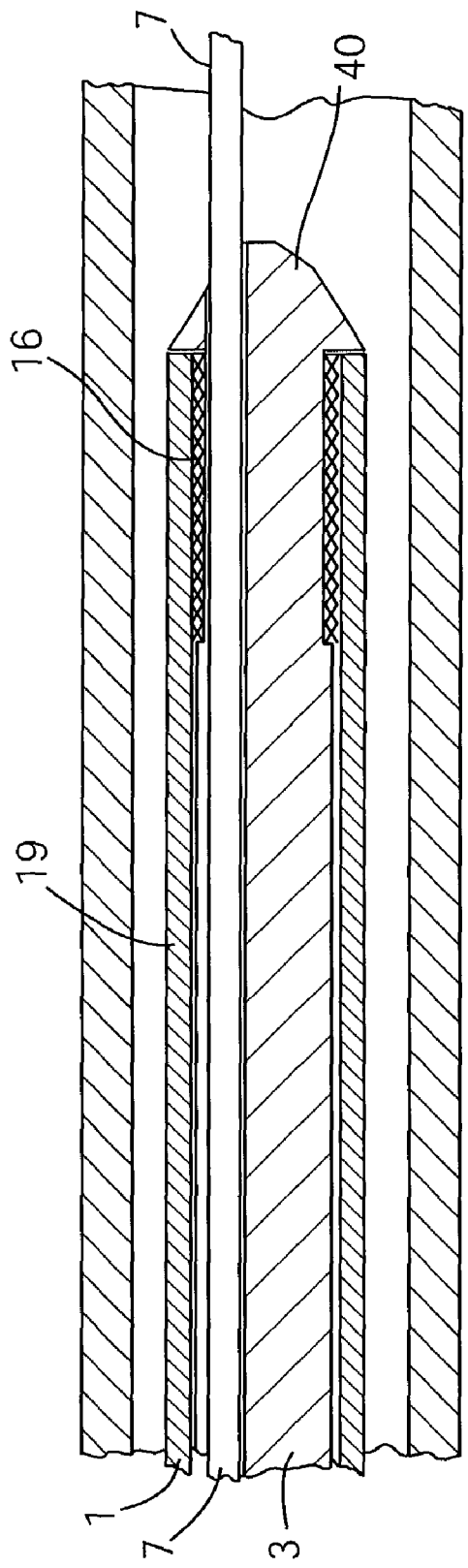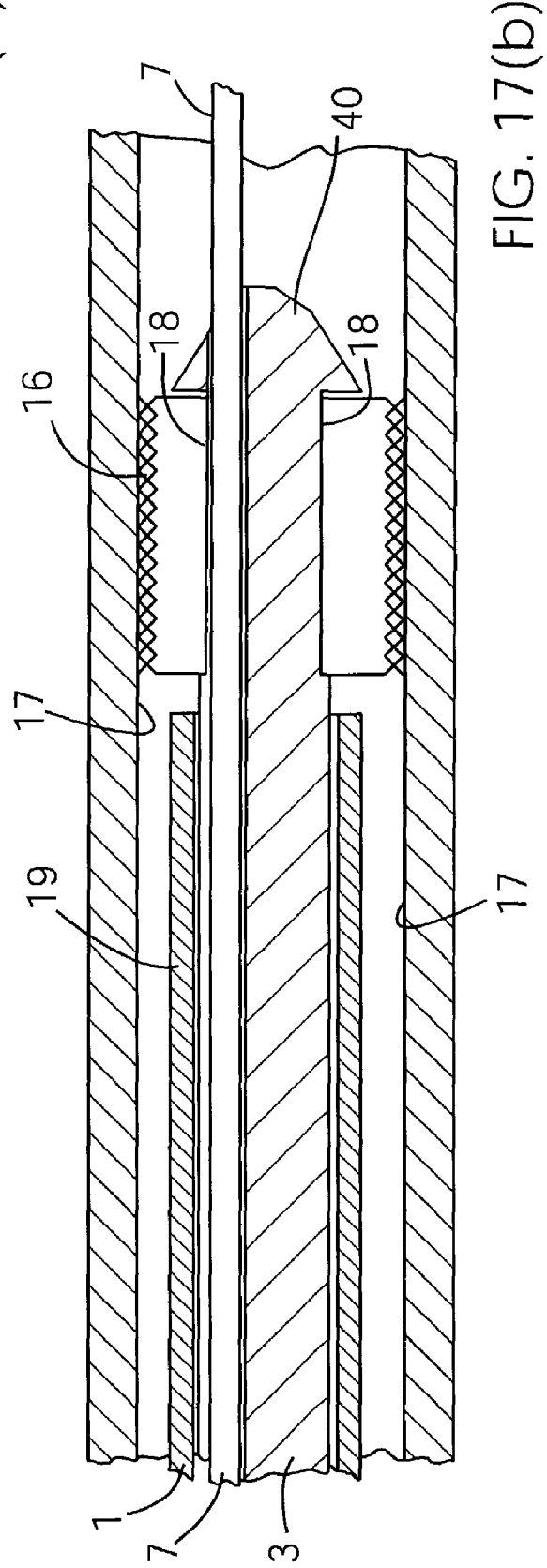
FIG. 17(a)
FIG. 17(b)

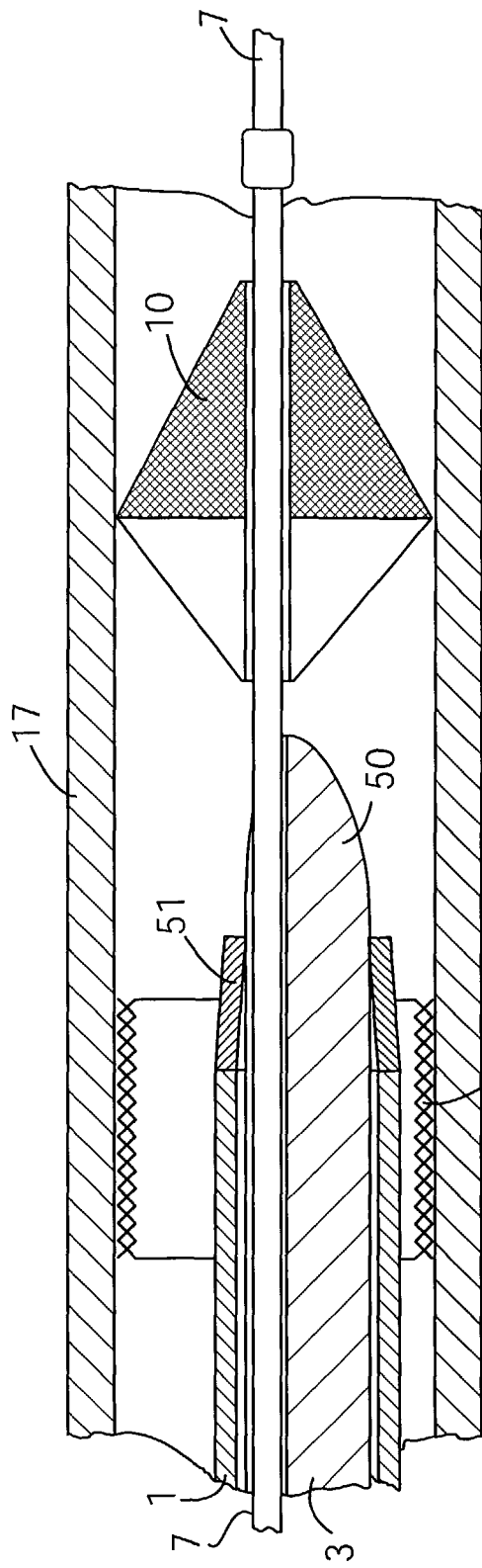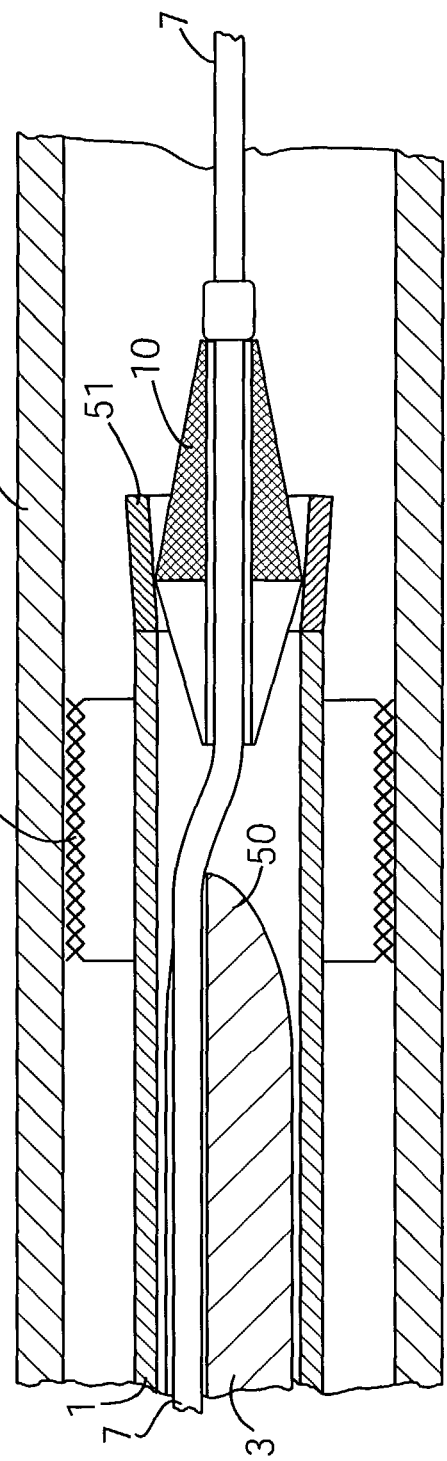
FIG. 18(a)
FIG. 18(b)

US 7,789,860 B2

CATHETER FOR DELIVERY AND/OR RETRIEVAL OF A MEDICAL DEVICE

CROSS-REFERENCE TO RELATED APPLICATIONS

This Application is related to, and claims the benefit of, the following patent applications, namely: Irish Patent Application No. 2001/0591, filed Jun. 27, 2001; and U.S. Patent Application No. 60/301,820, filed Jul. 2, 2001; all of which are hereby incorporated herein by reference in their entirety.

FIELD OF THE INVENTION

Many intravascular catheter designs require that one tube move relative to another. Typically an outer tube may provide a reception space for a medical device during delivery or retrieval. The inner tube may provide a deployment function, or a centering function. Examples of such catheters include self-expanding stent delivery systems, filter delivery systems and retrieval catheters. In all these cases mechanical forces are transmitted from one end of the tube to the other. These forces may be tensile (pull), or compressive (push). Typically when a pull force is applied to one of the tubes, a reaction push force is set up in the other and relative movement takes place (and vice versa). Typically a guidewire lumen is provided through the center of the inner tube.

Many catheter systems are provided in rapid exchange format as these systems are considered to be easier to use by many clinicians. This requires that the guidewire travel from the inner lumen through the wall of the inner tube and subsequently through the wall of the outer tube. The catheter construction must allow relative movement of the inner and outer tubes in this area. This problem is typically solved by providing a slot in the wall of either the inner of the outer and an exit port in the wall of the other. The slot must be at least the length of the longest anticipated stroke of the inner relative to the outer (or vice versa).

Such systems have a number of serious limitations associated with the slot. Firstly, the presence of a slot in the shaft significantly compromises the mechanical integrity of the shaft. Slots cut into the walls of tubes are very prone to kinking, are unable to resist torque loading and often have a tendency to collapse inwardly. The reduction in mechanical properties is contributed to in part by the reduction in cross section but also by the lack of self-support that is integral to a tube. These problems are particularly evident when the wall of the tube is thin.

In general the guidewire exit port location of catheters for rapid exchange use is a transition zone where the catheter is prone to kinking and damage due to a non-linear transition from the distal to proximal section of the catheter. The incorporation of a slot also affects the overall symmetry of the catheter and therefore will generally be the location where any unwanted deformation will be initiated.

There is therefore a need for an improved construction of catheter which will overcome at least some of these problems.

SUMMARY OF THE INVENTION

According to the invention there is provided a system for the delivery and/or retrieval of a medical device comprising:
 a catheter including an elongate shaft;
 the elongate shaft having a proximal end, a distal end and a wall defining a shaft lumen; and
 an inner solid member extending through the shaft lumen; the solid member defining a surface pathway to direct a guidewire from a distal guidewire port to a proximal guidewire port.

In this specification the inner member or pusher is defined as being solid if the guidewire pathway is defined external to the body of the member, and the sum of its cross sectional area and the cross sectional area of the guidewire are substantially equal to the cross sectional area of a rod of the same maximum diameter as the member.

In one embodiment of the invention the proximal guidewire port is positioned a substantial distance distal of the proximal end of the shaft. Preferably the guidewire pathway is offset from a longitudinal axis of at least a portion of the elongate shaft.

The guidewire pathway may be partially defined by an inner surface of the elongate shaft. The guidewire pathway may be partially defined by a longitudinally extending portion of the surface of the solid member. The guidewire pathway may be partially open along a substantial portion of its length.

In one case the solid member is slideably translatable relative to the elongate shaft. In another case the solid member is slideably translatable relative to a guidewire.

The catheter preferably comprises a reception space at the distal end of the shaft. Ideally the reception space is offset relative to the shaft of the catheter. The reception space may be a pod. Preferably the pod is thin walled. Most preferably the pod is reinforced.

In another embodiment of the invention the inner solid member is reinforced. The reinforcement may be a metal. Preferably the metal is at least partially comprised of one or more of titanium, vanadium, molybdenum, iron, chromium and nickel.

The reinforcement may comprise at least one wire. Preferably the wire is of stainless steel.

The reinforcement may be a fiber. Preferably the fiber is glass, Kevlar, graphite, carbon or a polymeric fiber.

In one case the reinforcement is disposed coaxial to the center of area of the solid member.

Desirably the solid member comprises an abutment surface at its distal end. Preferably the abutment surface is engagable with a medical device for deployment of the device.

In a preferred embodiment a tip is provided at the distal end of the inner member. The tip may be integral with the inner member. Preferably the tip provides a smooth transition between the guidewire and the catheter shaft. Ideally the tip defines a pathway through the medical device. Most preferably the tip is of a soft atraumatic material.

The lumen of a medical device in the reception space is preferably interfaced with the guidewire surface pathway of the solid member. In one case the interface comprises a ramp feature. In another case the interface comprises a portion of a funnel.

Ideally the cross sectional area of the inner member added to the cross sectional area of the guidewire comprise substantially the cross sectional area of the inner lumen of the shaft.

In another embodiment of the invention a marker band is provided at the distal end of the inner solid shaft. The marker band may be attached to the inner shaft. Preferably the marker band is solid in construction.

In a further case the solid member is rotationally fixed relative to the elongate shaft. The system may comprise a key to prevent rotational movement. In one embodiment the key is provided in a portion of the outer shaft. In another embodiment the key is provided at the guidewire exit port. Preferably a ramp is provided at the exit port and the ramp defines the key. In a further embodiment the key is provided in a handle portion of the shaft.

In a particularly preferred embodiment the guidewire exit port comprises an opening in the wall of the elongate shaft. Preferably the system comprises a ramp for guiding a guidewire to the exit port. Ideally the ramp comprises a tongue-like segment extending inwardly from the exit port. Most preferably the tongue extends into the surface guidewire pathway in the inner member. The tongue may substantially fill the cross section of the surface guidewire pathway. Preferably the ramp surface has a cylindrical aspect. The tip may be offset relative to the guidewire.

The exit port is preferably sized so as to provide clearance to the guidewire.

In one case the guidewire exit port is generally angulated in the direction of guidewire movement.

In one embodiment of the invention the catheter is a filter delivery catheter. Preferably the shaft has a distal pod defining a reception space for a filter.

In another embodiment the catheter is a stent delivery catheter. Preferably the shaft has a reception space at the distal end for reception of a stent. Most preferably the inner member extends through a lumen defined by the stent. Ideally the inner member terminates in a distal tip.

In a further embodiment the catheter is a filter retrieval catheter. Preferably the shaft has a distal reception space for reception of a retrieved filter. The inner member may extend through the reception space during positioning of the catheter for filter retrieval. Preferably the inner member projects distally of the distal end of the shaft to provide centring.

These and other problems are solved by the catheter designs of this invention. Rapid exchange catheters are provided that deliver all of the advantages of a dual tube systems without the drawbacks of these systems when configured in a rapid exchange slot and hole format.

The designs of this invention provide a solid inner member and an outer tube with a discrete exit port. A guidewire surface pathway is provided that guides the guidewire to the exit port. A variety of exit port configurations are possible.

The fact that the inner member is solid provides a range of advantages not available with tubular systems. Firstly, the inner member maintains cross-sectional area over its entire length. This ensures that it has no mechanical weak points and is homogenous in its properties over its length. Solid shafts are not susceptible to kinking. Solid shafts provide excellent push and tensile transmission. Solid shafts have lower bending stiffness than tubes of the same cross-sectional area due to their lower second moment of area.

The catheters of this invention allow relative movement between an outer catheter and inner pusher without the inclusion of a slot in either the inner or outer elements. A guidewire rapid exchange exit port is included in the outer catheter. This exit port is sized to accommodate the exit of the guidewire. The exit port preferably has a tapering aspect to minimize the force required to manipulate the guidewire out through the exit port.

A very important feature of the inner members of the invention is the fact that the material volume is concentrated close to the neutral axis of the inner member. This provides an excellent relationship between the push and trackability properties of the inner member. Push properties tend to be dominated by the cross sectional area of the member and the material properties. Trackability properties depend strongly on the distance the material is spread from the neutral axis ($2^{nd}$ moment of area) and the material properties. Solid members are advantageous because the presence of a lumen in the center of a member results in material being distributed farther from the neutral axis.

Another advantage is derived from the fact that the surface area available for friction build up is minimized. Tubular systems have the disadvantage that movement of the inner relative to the outer and the guidewire generates significant frictional forces. This situation arises because the inner has a large surface area when its inner and outer surfaces are added together. This large surface area adds to the drag when the inner element is moved relative to the other parts of the system. Tubular systems also build up frictional forces with the guidewire. When the system is placed in a tortuous vessel the bending forces of the guidewire are applied directly to the surface of the inner. This sets up normal forces on the inner that do not affect the inner members of this invention.

Because the inner members of this invention are solid no inner frictional surface exists. Further more normal forces associated with the bending stiffness of the guidewire are not transmitted to the inner member since the guidewire is accommodated on the outer surface of the inner member.

The transmission of mechanical forces can be further optimized with this invention through the use of reinforcements. Because the guidewire has been moved from the central axis location it is now possible to incorporate reinforcing wires or fibers or members in that location. Reinforcements work particularly well with this invention as they can be placed very close to the neutral axis of the inner member irrespective of its plane of bending. Tubular elements require that reinforcements be placed in the walls of the tube. When push properties are desired metallic reinforcements such as wires are desirable. Solid wires or bundles of wires are excellent for transmitting push. Braided systems can be used to optimize torque.

Regardless of the type of reinforcement employed it is desirable that it be placed as close to the center of area of the cross section of the member as possible. Where it is not placed exactly on the center of area it should be centered over the center of area. It should be noted that the center of area is not the same as the central axis of the member. The presence of the surface guidewire pathway shifts the center of area very slightly. Centering reinforcements around the center of area ensures that the properties of the reinforced shaft are very homogenous.

When crossing a lesion with a device it is often advantageous to have the guidewire centrally located within the device and, in particular, the distal portion of the device which crosses the lesion first. The use of surface guidewire pathways can result in the guidewire being off center relative to outer shaft. In many situations this feature presents no difficulty and may even be advantageous to the manoeuvring of the catheter. Where it is required to maintain the guidewire central to the medical device at the distal end a number of guiding features may be provided.

The reception space at the distal end of the shaft may be offset relative to the shaft so as to ensure the alignment of the surface guidewire pathway with the central lumen of the medical device.

In another variation the distal end of the inner member may be provided with a discrete ramp that directs the wire from the central axis of the medical device to the surface guidewire pathway. A variety of ramp configurations are possible including a funnel, a ramp with a circular aspect or a tunnel style ramp.

A significant advantage of this invention is that relative movement of the inner member and the outer catheter does not affect the rapid exchange capability in any way. The surface pathway provided in the inner ensures that the guidewire is in contact with the surface of the outer. This ensures that only small lateral movement is required to direct the guidewire to exit the exit port. This feature ensures that the guidewire movement of the catheter is good. The orientation of the surface guidewire pathway is maintained relative to the exit port so as to ensure that the end of the guidewire is presented to the exit port in the correct orientation when the catheter is being loaded onto a guidewire. This orientation needs to be maintained only in the area of the exit port. A number of features are provided per this invention to ensure that orientation is maintained.

In one embodiment a keying arrangement is provided in the proximal section of the catheter. In one variation this key is provided on the inner surface of the outer and engages the surface pathway proximal to the exit port. This key may also be used to provide an exit ramp at the exit port.

In another variation the exit port ramp feature engages the surface guidewire pathway and prevents relative rotational movement of the inner and outer.

In yet another arrangement the keying function is located in the handle area. This system has the advantage that the user cannot attempt to rotate one element relative to the others and is preferred for this reason. Indeed, more than one keying feature can be used simultaneously.

An important feature of all these systems is that they do not inhibit longitudinal movement of the two members.

BRIEF DESCRIPTION OF THE DRAWINGS

The invention will be more clearly understood from the following description thereof given by way of example only, in which:

FIG. 1 is an isometric view of a portion of a catheter according to the invention;

FIG. 2 is a cross sectional view on the plane A of the catheter of FIG. 1;.

FIG. 3 is a cross sectional view on the plane B of the catheter of FIG. 1;.

FIGS. 7 and 8 are detailed cross-sectional views of a rapid exchange exit port region of the catheter;

FIG. 9 is a cross-sectional view on the line A of FIG. 8;

FIG. 10 is a cross-sectional view on the line A1 of FIG. 8;

FIG. 16(a) is a cross-sectional view of a catheter containing a stent in a pre-deployment or delivery configuration;

FIG. 16(b) is a cross-sectional view of the catheter of FIG. 16(a) with a stent in a deployed configuration;

FIG. 17(a) is a cross-sectional view of another catheter containing a stent device in a pre-deployment or delivery configuration;

FIG. 17(b) is a cross-sectional view of the catheter of FIG. 17(a) with a stent in a deployed configuration;

FIG. 18(a) is a cross-sectional view of a filter retrieval catheter in a pre-retrieval configuration;

FIG. 18(b) is a cross-sectional view of the catheter of FIG. 18(a) with a filter in a retrieved configuration;

DETAILED DESCRIPTION

Figure 4:
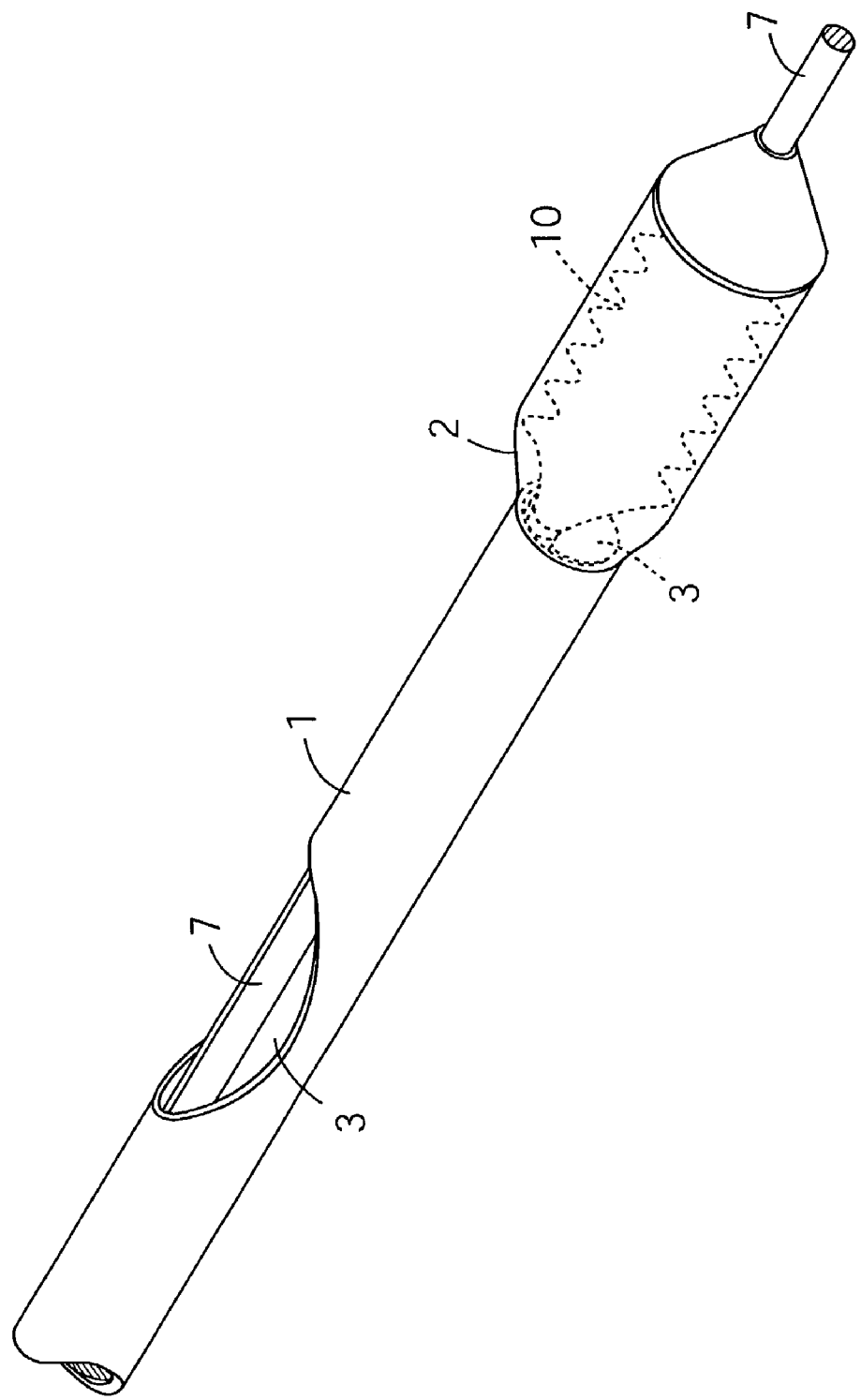
FIG. 4 is a perspective view of the catheter with a filter in a pre-deployment or delivery configuration.

Referring to FIGS. 1 to 3 there is illustrated a catheter suitable for the delivery of a medical device such as a stent or a filter. The catheter has an outer shaft 1 with a distal end and a proximal end. The distal end comprises a pod 2 that provides a reception space for a medical device. The catheter has an inner shaft 3 comprising a solid rod 5, a surface guidewire pathway 4 for a guidewire 7. The inner shaft defines an abutment surface 9 at its distal end. The guidewire pathway 4 extends longitudinally and is configured so as to accommodate the guidewire 7. The abutment surface 9 from the pod 2 is configured so as to engage with a medical device to achieve deployment of the medical device from the pod 2. In FIGS. 1 to 4 the catheter is shown in a deployed configuration. In this deployed configuration the distal end of the inner shaft 3 is in an advanced position relative to the pod 2. The outer shaft 1 further comprises an exit port 8 where the guidewire exits the catheter in a rapid exchange manner. It will be noticed that the pod 2 is shown offset relative to the shaft 1. This offset feature ensures that the central axis of the medical device is in alignment with the surface guidewire pathway 4.

FIG. 2 shows a cross sectional view of the catheter in the region of the pod 2. This view shows the guidewire 7 located in the pathway 4 of the inner shaft 3. It will be noticed however that the guidewire 7 is positioned centrally relative to the pod 2. This is achieved through the offset aspect of the pod 2 relative to the shaft 1.

FIG. 3 shows a cross sectional view of the catheter proximal to the exit port 8. The outer shaft is shown in a concentric arrangement with the solid inner shaft 5.

An isometric view of the rapid exchange technology of the invention is shown applied to a filter delivery system in FIG. 4. The guidewire 7 is shown protruding from the distal end of a filter 10. The filter 10 is in a collapsed or wrapped down configuration in the pod 2. A proximal end of the filter 10 is in abutment with the distal end of the inner member 3 such that a guidewire lumen of the filter is in alignment with the guidewire surface pathway 4. The offset pod 2 facilitates this alignment.

Figure 5:
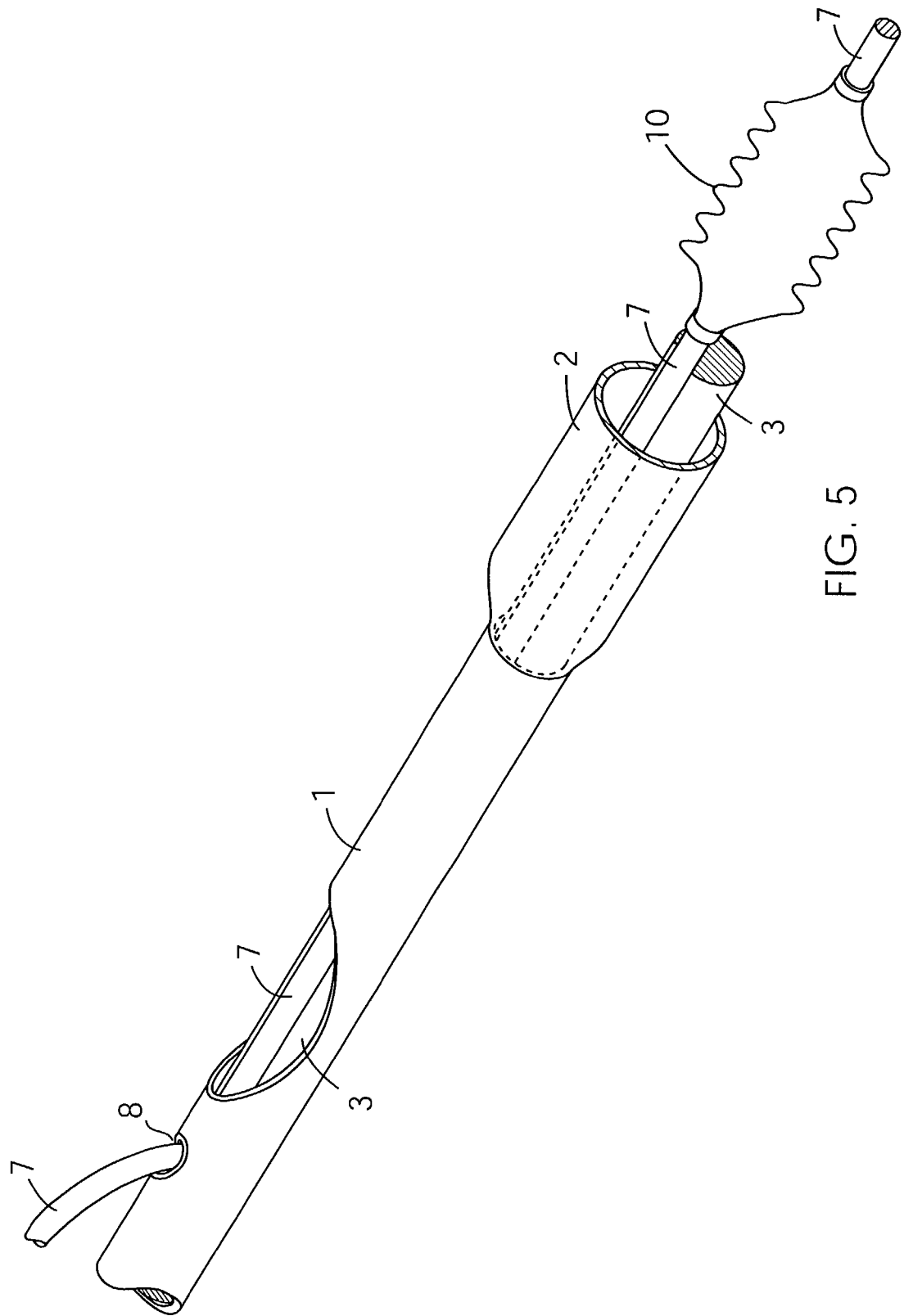
FIG. 5 is a perspective view of the catheter with a filter in a deployed configuration.

Another isometric view of the rapid exchange filter delivery system is shown in FIG. 5 in which the system is illustrated with the filter 10 in the deployed configuration. The inner shaft member 3 is in its advanced position and in so advancing the filter 10 is deployed. Alternatively, the catheter shaft and pod can be retracted to achieve filter delivery. It will be apparent that the rapid exchange filter delivery system of this invention can be applied to filter systems that are fixed on the wire or to filter systems wherein the filter can move independently of the wire.

Figure 6A:
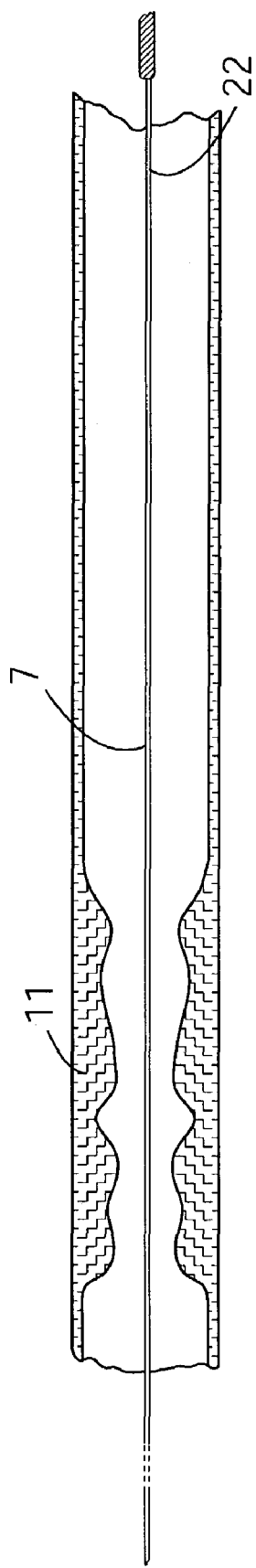
FIG. 6(a) is a cross sectional view of a vessel with a lesion which has been crossed with a guidewire.
Figure 6E:
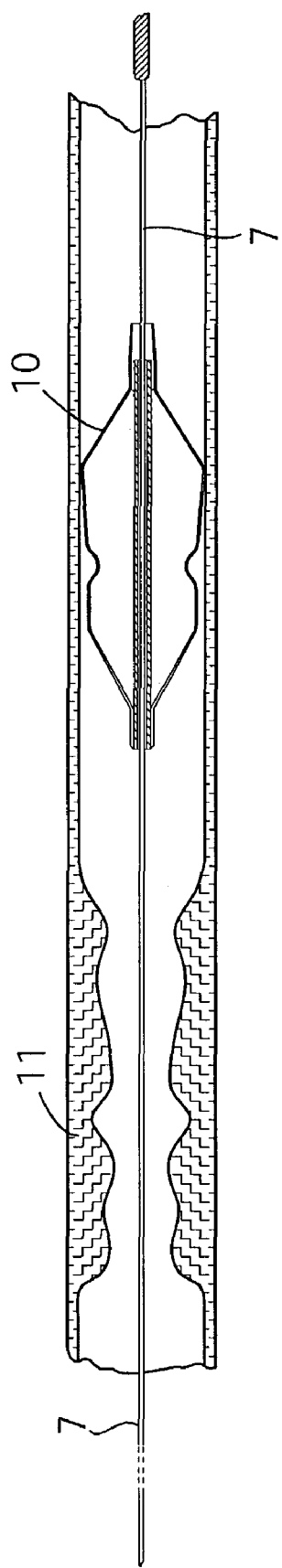
FIG. 6(e) illustrates a filter deployed on a guidewire distal to a lesion site.
Figure 6B:
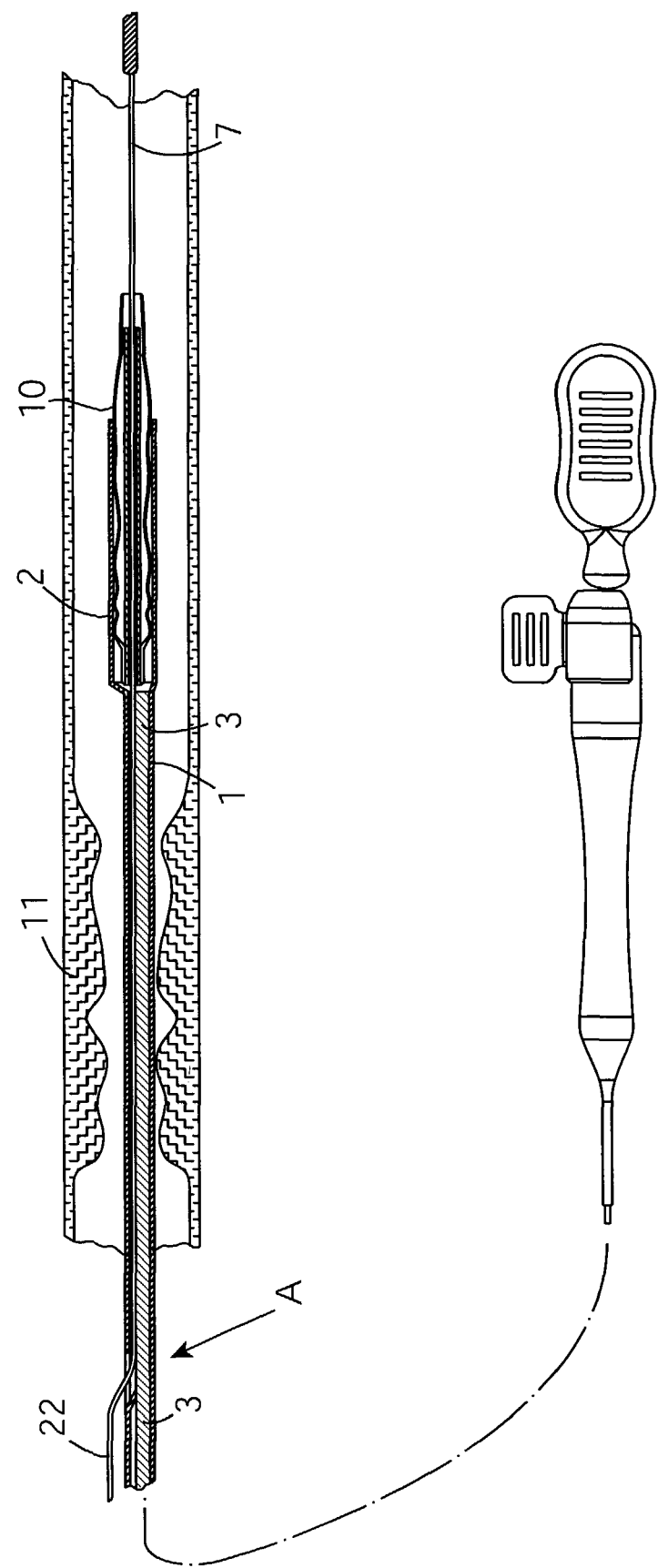
FIG. 6(b) illustrates a delivery catheter containing a filter which has been passed over a guidewire to an intended vascular site ready for deployment.

FIG. 6*a* shows a vascular lesion 11 in a vessel which has been crossed with a guidewire 7. The guidewire 7 is in a position to receive a catheter, as illustrated in FIG. 6*b*. This schematic illustration shows a catheter according to the invention which contains a filter 10 in a wrapped down configuration in the pod 2. The catheter is shown having tracked over the guidewire 7 and at a position distal to a lesion 11 ready for deployment.

Figure 6C:
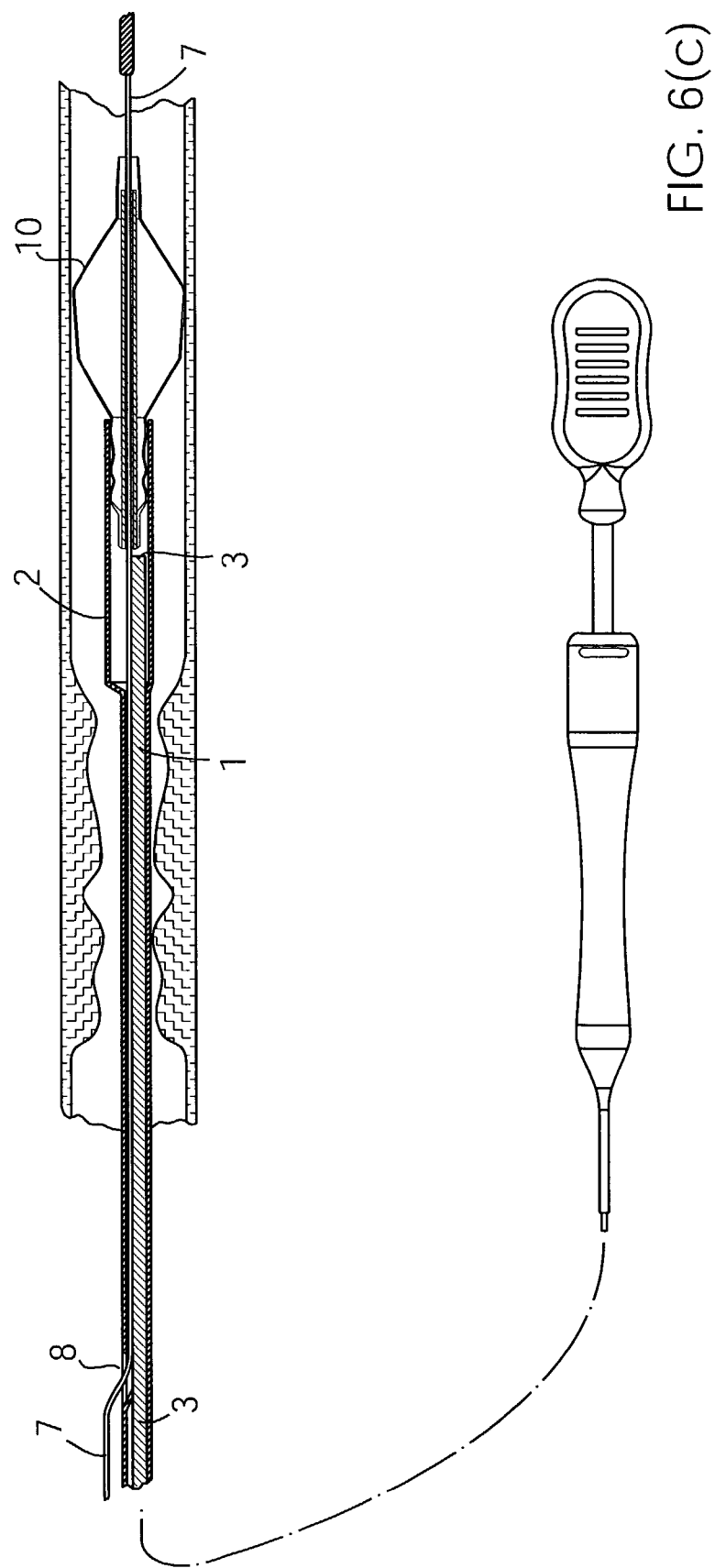
FIG. 6(c) illustrates a partially deployed filter exiting the catheter at the deployment site.

Deployment of the filter 10 is shown in FIG. 6*c*. The schematic captures the deployment at a stage where the filter 10 is partially deployed from catheter pod 2. The solid inner pusher rod 3 is engaged with the most proximal portion of the filter 10. The abutment surface 9 defines the plane of engagement with the proximal end of the filter 10 which allows the required forces to be transmitted between the solid pusher rod 3 and the filter 10 to enable filter delivery. It should be noted that the solid pusher rod 3 is a very effective force transmitter and may have other applications where a force is required to deploy a medical device from a reception space or indeed where it is necessary to retrieve a device into a reception space.

Figure 6D:
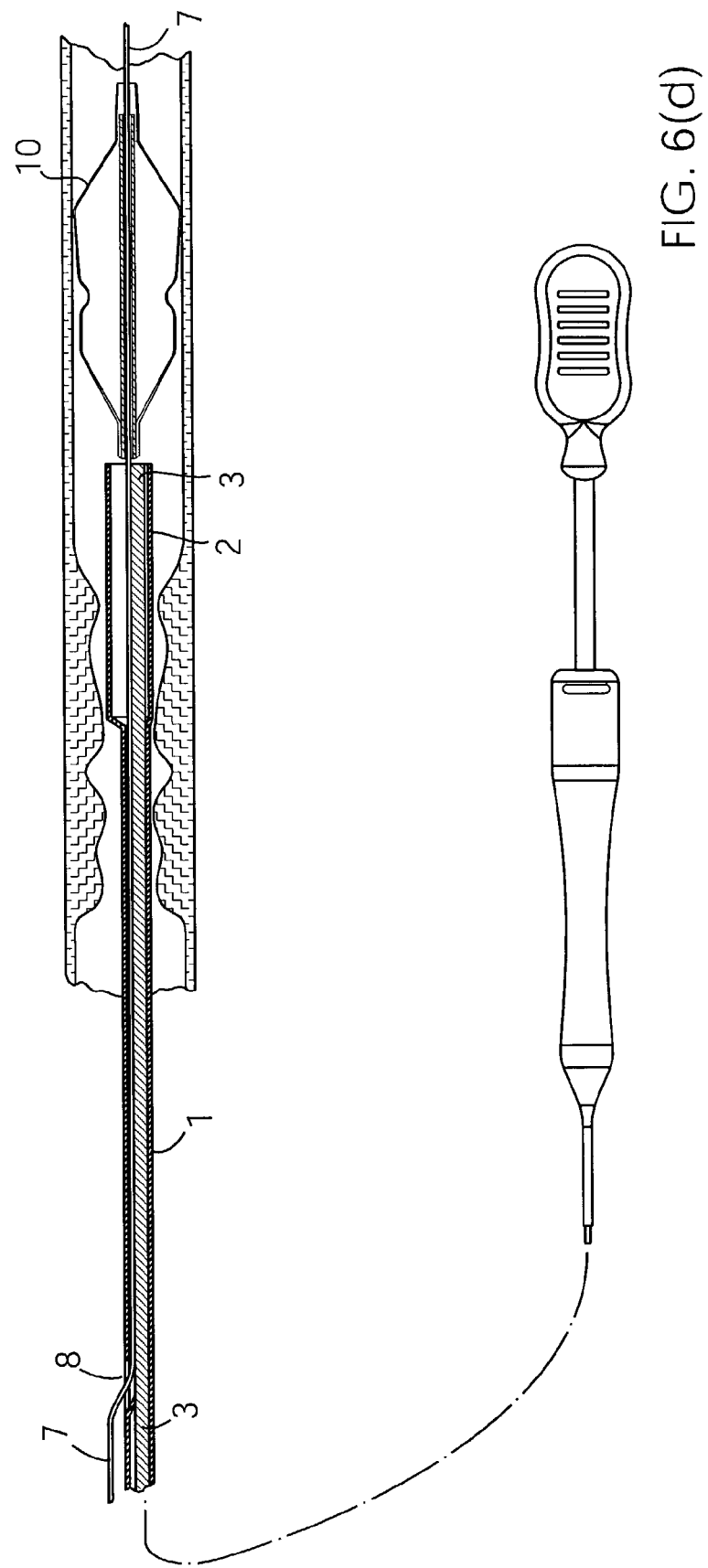
FIG. 6(d) illustrates the filter in its deployed state at an intended site distal to a lesion.
Figure 7:
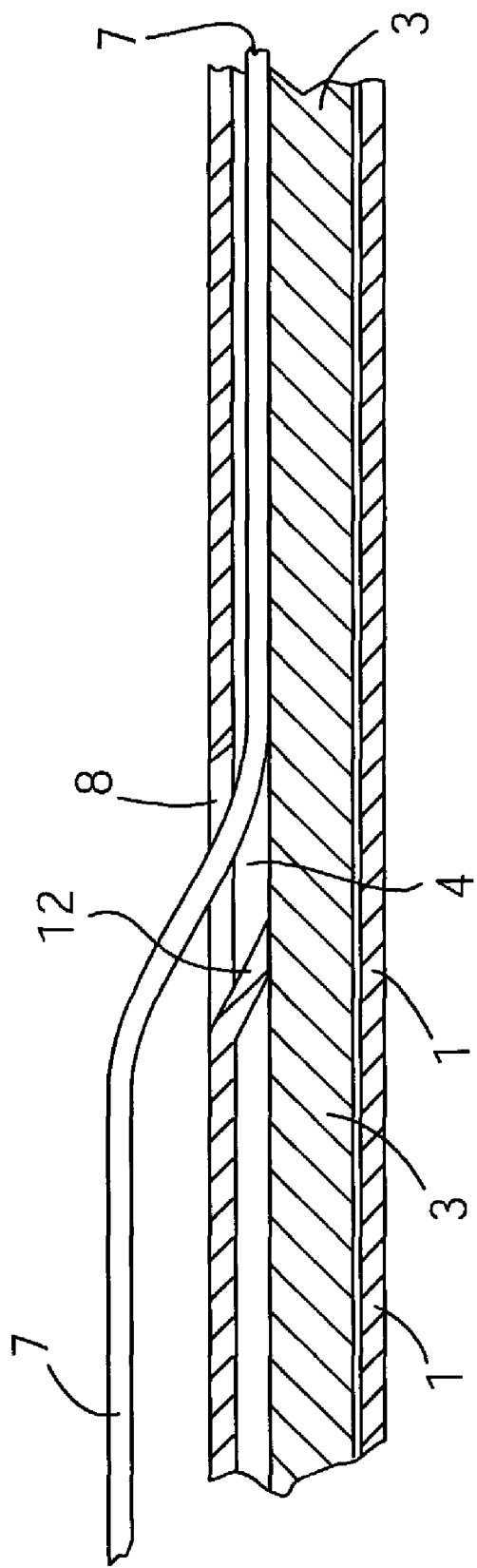

FIG. 6*d* shows the filter 10 after complete deployment at the intended vascular site with the delivery catheter shown proximally awaiting removal from the vasculature. FIG. 4*e* shows a filter deployed on a guidewire distal to a lesion site with the delivery catheter removed from the vasculature.

The catheter in the region of the rapid exchange exit port is shown in greater detail in cross-section in FIGS. 7 to 10. The guidewire 7 is shown alongside the guidewire surface path 4 distal to the exit port 8. A ramp feature 12 is shown which directs the guidewire away from the guidewire surface path and through the exit port in the outer catheter 1.

Figure 11:
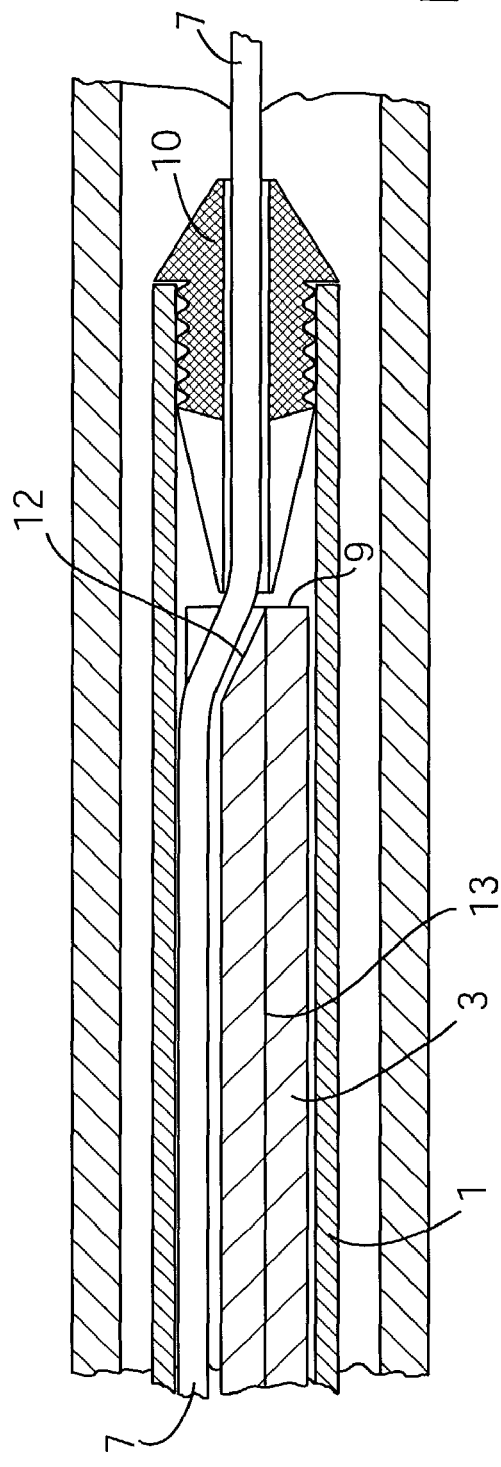
FIG. 11 is a cross-sectional view of a distal end of the catheter showing a ramp that directs a guidewire from the central axis of a medical device and along a guidewire surface path.

Another configuration of filter delivery system is shown in FIG. 11. In this embodiment the distal end of the shaft 1 comprises the filter reception space 2. It will be noted in this embodiment that there is no off set to the pod 2. Instead, the guidewire 6 is directed to the surface guidewire pathway 4 by means of a ramp 12 at the distal end of the inner member 3. A reinforcement 13 is shown on the centre of area of the cross section of the inner member 3. The reinforcement 13 provides push transmission for the filter deployment action. In one embodiment the reinforcement 13 is manufactured from a metal. In another the reinforcement 13 contains fibre reinforcement. Preferred metals include iron, nickel, chromium, molybdenum, vanadium, titanium or alloys containing one or more of the above. Stainless steels are the most preferred metallic reinforcements. Fibre reinforcements include Kevlar, glass, graphite, carbon, polymer fibres and mixtures of the above. The reinforcement may also have sensory capabilities inbuilt to increase functionality.

Figure 12:
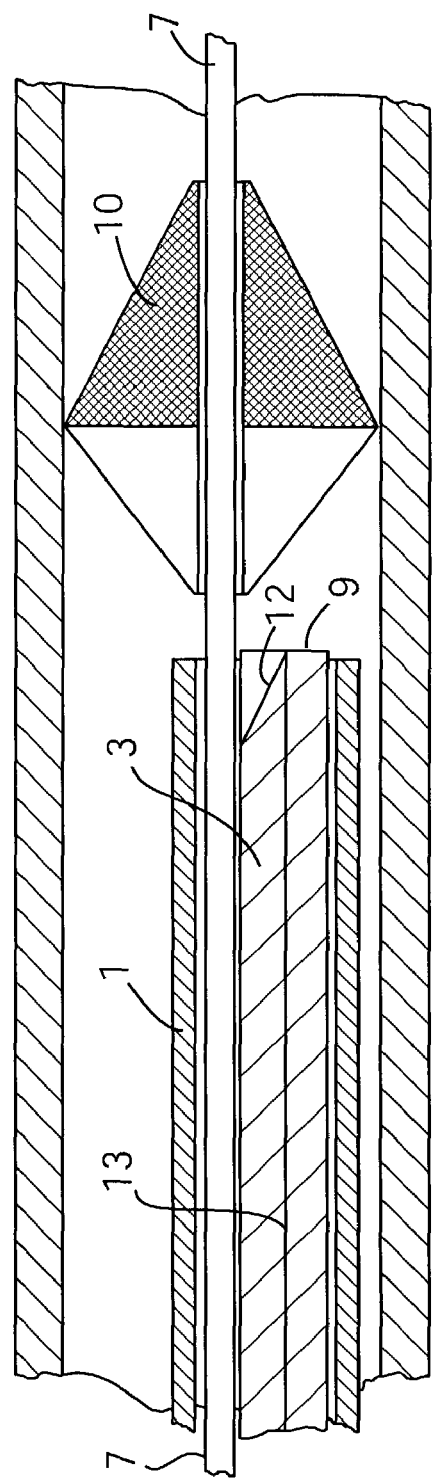
FIG. 12 is a cross-sectional view of a distal end of a catheter showing a guidewire extending along a guidewire surface path.

FIG. 12 shows the deployed configuration of the system of 11. The inner member 3 has an abutment surface 9 at its distal end that engages the filter for deployment.

Figure 13:
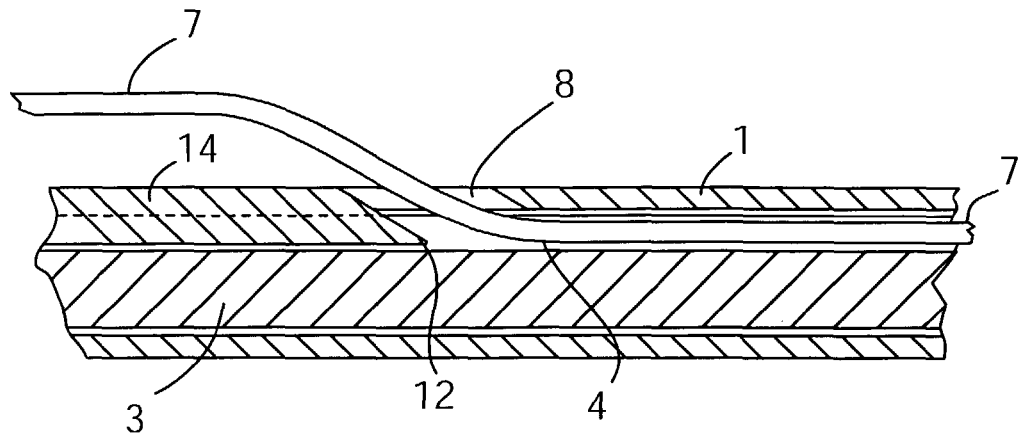
FIG. 13 is a cross-sectional view of a detail of a catheter showing a keying arrangement provided in the proximal section of the catheter, a key being provided on the inner surface of the outer and engaging a surface pathway proximal to the exit port. This key may also be used to provide an exit ramp at the exit port.

FIG. 13 shows an alternative means for allowing the guidewire 6 to be directed from its side by side contact with the guidewire surface path 4 and exit the outer catheter 1 via the exit port 8. This is facilitated by means of a keying arrangement 14 which is provided on the inner surface of the outer catheter 1 and which engages a surface pathway proximal to the exit port 8. Another feature of the key 14 is that it engages the surface guidewire pathway 4 and prevents relative rotational movement of the inner and outer. The key 14 may also be used to provide an exit ramp 12 at the exit port 8.

Figure 14:
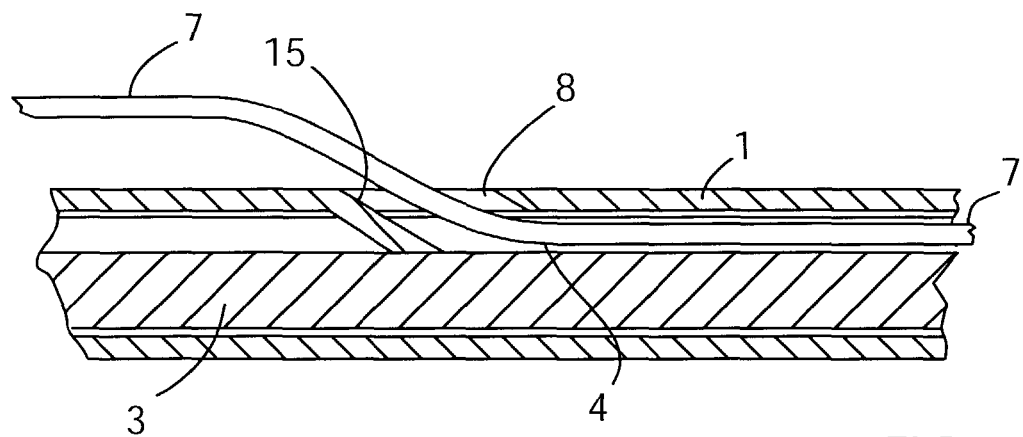
FIGS. 14 and 15 are cross-sectional views of a detail of a catheter showing an inwardly directed tongue on the outer catheter, the tongue engaging a surface pathway proximal to the exit port, this tongue may also be used to provide the exit ramp at the exit port.
Figure 15:
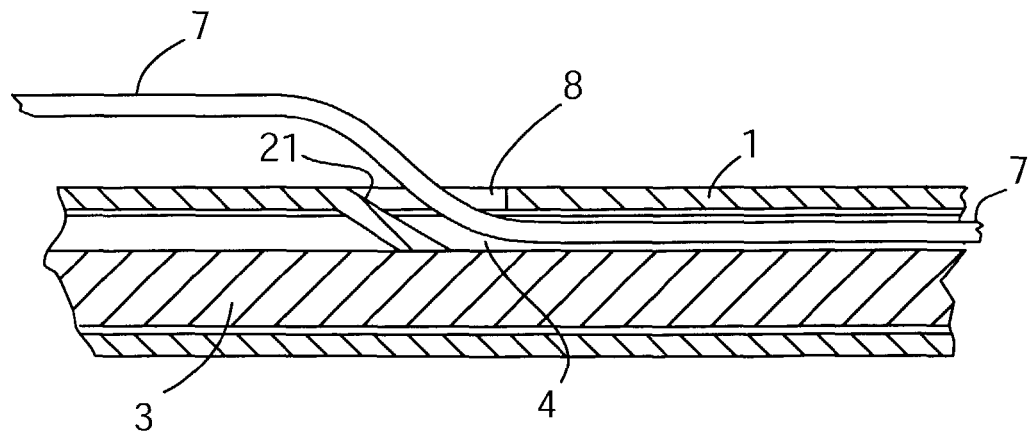

FIG. 14 shows an inwardly directed tongue 15 on the outer catheter 1. The tongue 15 engages a surface pathway proximal to the exit port 8. The tongue 15 may also be used to provide an exit ramp at the exit port 8. In FIG. 5 there is illustrated a tongue 21 which may be used to provide an exit ramp and is of a generally cylindrical aspect.

In yet another arrangement the keying function is located in the handle area. This system has the advantage that the user cannot attempt to rotate one element relative to the others and is preferred for this reason. Indeed more than one keying feature can be used simultaneously.

An important feature of all these systems is that they do not inhibit longitudinal movement of the two members.

The rapid exchange catheter technology of this invention may be configured as a stent delivery system as illustrated in FIGS. 16(*a*) and 16(*b*). A self expanding stent 16 is restrained in a reception space at the distal end of the catheter shaft 1. The inner shaft 3 is of solid cross section and contains a surface guidewire pathway 4. The distal end 9 of the inner shaft 3 abuts the proximal end of the stent 16. A tip section 30 is attached to the distal end of the inner shaft. The tip 30 provides a pathway 31 for the guidewire 7 through the body of the stent 16 and guides the guidewire 6 to the surface guidewire pathway of the inner member. The tip 30 further provides a smooth transition between the guidewire 7 and the catheter at its distal end. It will be appreciated that the inner member 3 of this configuration might also be advantageously reinforced to provide push.

A further advantage of this invention is the possibility of using solid markerbands. Because the inner member has no lumens it is possible to attach solid marker bands to the distal end of the shaft ends. This provides exceptionally high levels of visibility of the marker bands.

The stent delivery system of FIG. 16*a* is shown in the deployed configuration in FIG. 16*b*. The outer shaft is shown in the retracted position relative to the inner member 3 and the stent 16 deployed in apposition with the vessel 17.

An alternative stent delivery configuration is shown in FIGS. 17*a* and 17*b*. In this embodiment the inner member 3 comprises a solid shaft with a surface guidewire pathway 4. The solid shaft 3 continues distally to provide a distal tip 40 and contains a recess 18 in the region of the stent 16. The guidewire surface 4 may be in direct contact with the inner surface of elements of the stent 16 as the stent partially defines the guidewire pathway. The stent delivery system is shown in the deployed configuration in FIG. 17*b*. An outer shaft 19 is shown in the retracted position relative to the inner member 3 and the stent 16 is in apposition with a vessel 17.

Referring to FIGS. 18*a* and 18*b* the rapid exchange technology of this invention is illustrated configured as a retrieval system. In this embodiment a solid inner member 3 has a tip 50 that provides a centring function at its distal end. In doing so it provides a smooth transition for crossing stents and lesions. The guidewire 7 is offset relative to the main shaft 1. This has an important advantage compared to conventional retrieval systems in that it can better negotiate stented lesions. Crossing stented lesions is one of the most important design functions of filter retrieval systems. With the trend towards segmented stents crossing implanted stents is becoming increasingly difficult. Segmented stents present a particular problem in that crowns can project into the lumen of the vessel. These crowns can easily snag on a passing retrieval catheter. It can be very difficult to free a retrieval system from such a snag if the vessel is curved as lateral forces continue to push the system onto the crown. This problem can be overcome per this invention due to the eccentric nature of the catheter. By simply torqueing the entire catheter the eccentric tip 50 will relieve a snag and allow crossing by providing a slight lateral movement.

The retrieval system of FIG. 18a is shown with the filter 10 retrieved in FIG. 18b with the filter 10 retrieved into the reception space 2 at the distal end. The distal end of the retrieval catheter is shown with an expansile tip 51. In one embodiment the distal end 50 of the inner shaft 3 is made of a soft material and bends and deflects easily. This allows the tip 51 to deform slightly during retrieval so as to provide good guidewire movement.

Figure 19:
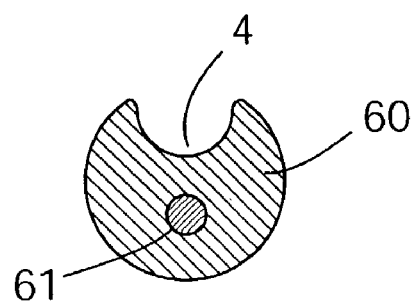
FIG. 19 is a cross-sectional view of a solid inner pusher containing a solid wire at its neutral axis.

FIG. 19 is a cross-sectional view of a solid inner pusher 60 containing a solid reinforcing wire 61 at its neutral axis. The pusher 60 has a guidewire pathway 4. Because the guidewire has been moved from the central axis location it is now possible to incorporate reinforcing wires or fibers or members in that location. Reinforcements work particularly well with this invention as they can be placed very close to the neutral axis of the inner member irrespective of its plane of bending. Tubular elements require that reinforcements be placed in the walls of the tube. When push properties are desired metallic reinforcements such as wires are desirable. Solid wires or bundles of wires are excellent for transmitting push. Braided systems can be used to optimize torque.

Figure 20:
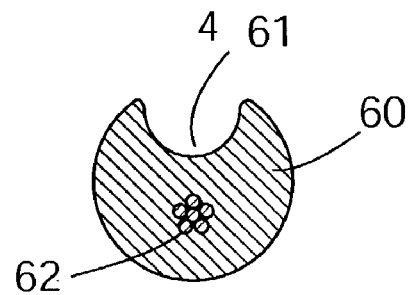
FIG. 20 is a cross-sectional view of a solid inner pusher containing a multi-filament wire at its neutral axis.
Figure 21:
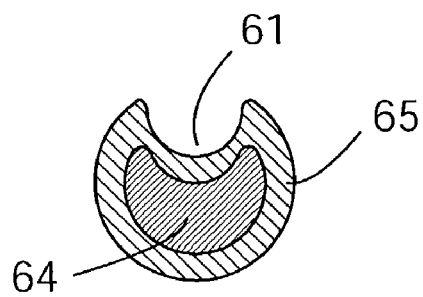
FIG. 21 is a cross-sectional view of a co-extruded solid inner pusher.

Which ever reinforcement is employed it is desirable that it be placed as close to the center of area of the cross section of the member as possible. Where it is not placed exactly on the center of area it should be centered over the center of area. It should be noted that the center of area is not the same as the central axis of the member. The presence of the surface guidewire pathway 4 shifts the center of area very slightly. Centering reinforcements around the center of area ensures that the properties of the reinforced shaft are very homogenous. FIG. 20 shows a cross-sectional view of a solid inner pusher 60 containing a multifilament wire 62 at its neutral axis. FIG. 21 shows a co-extruded solid pusher with a solid inner of material 64 with a solid outer of material 65. The relative amounts of materials 64 or 65 can be varied to tailor the stiffness and frictional characteristics required by the pusher. The co-extrusions could also me multi-layered or include reinforcement.

Figure 22:
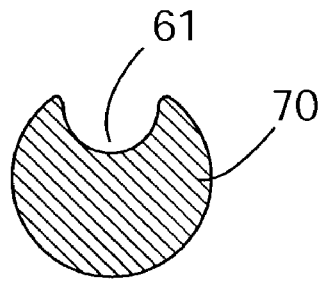
FIG. 22 is a cross-sectional view of an inner pusher as a solid member.

FIG. 22 shows a solid inner member 70 that has been manufactured from a tube. The solid member 70 is formed by placing a tube in a heated die of the appropriate form and pressure is applied so as to reform the material to the cross section of FIG. 22.

The invention is not limited to the embodiments hereinbefore described which may be varied in detail.

The invention claimed is:

1. A system for the delivery and/or retrieval of a medical device comprising:
    a guidewire;
    a catheter including an elongate tubular shaft;
    the elongate tubular shaft having a proximal end, a distal end and a wall defining a tubular shaft lumen; and
    an inner solid rod member extending through an entire length of the shaft lumen;
    the inner solid rod member defining a longitudinally extending surface pathway in the surface of the solid rod member to direct the guidewire from a distal guidewire port to a proximal guidewire port.

2. A system as claimed in claim 1 wherein the proximal guidewire port is positioned a substantial distance distal of the proximal end of the shaft.

3. A system as claimed in claim 1 wherein the guidewire pathway is offset from a longitudinal axis of at least a portion of the elongate shaft.

4. A system as claimed in claim 1 wherein the guidewire pathway is partially defined by an inner surface of the elongate shaft.

5. A system as claimed in claim 1 wherein the guidewire pathway is partially defined by a longitudinally extending portion of the surface of the inner solid rod member.

6. A system as claimed in claim 1 wherein the guidewire pathway is partially open along a substantial portion of its length.

7. A system as claimed in claim 1 wherein the inner solid rod member is slideably translatable relative to the elongate shaft.

8. A system as claimed in claim 1 wherein the inner solid rod member is slideably translatable relative to a guidewire.

9. A system as claimed in claim 1 wherein the catheter comprises a reception space at the distal end of the shaft.

10. A system as claimed in claim 9 wherein the reception space is offset relative to the shaft of the catheter.

11. A system as claimed in claim 9 wherein the reception space is a pod.

12. A system as claimed in claim 11 wherein the pod is thin walled.

13. A system as claimed in claim 11 wherein the pod is reinforced.

14. A system as claimed in claim 1 wherein the inner solid member is reinforced.

15. A system as claimed in claim 14 wherein the reinforcement is a metal.

16. A system as claimed in claim 15 wherein the metal is at least partially comprised of one or more of titanium, vanadium, molybdenum, iron, chromium and nickel.

17. A system as claimed in claim 14 wherein the reinforcement comprises at least one wire.

18. A system as claimed in claim 17 wherein the wire is of stainless steel.

19. A system as claimed in claim 14 wherein the reinforcement is a fiber.

20. A system as claimed in claim 19 wherein the fiber is glass, Kevlar, graphite, carbon or a polymeric fiber.

21. A system as claimed in claim 14 wherein the reinforcement is disposed coaxial to the center of area of the solid member.

22. A system as claimed in claim 1 wherein the inner solid rod member comprises an abutment surface at its distal end.

23. A system as claimed in claim 22 wherein the abutment surface is engagable with a medical device for deployment of the device.

24. A system as claimed of claim 1 wherein a tip is provided at the distal end of the inner solid rod member.

25. A system as claimed in claim 24 wherein the tip is integral with the inner solid rod member.

26. A system as claimed in claim 24 wherein the tip provides a smooth transition between the guidewire and the catheter.

27. A system as claimed in claim 24 wherein the tip defines a pathway through the medical device.

28. A system as claimed in claim 24 wherein the tip is of a soft atraumatic material.

29. A system as claimed in claim 10 wherein a medical device in the reception space is interfaced with the surface pathway of the inner solid rod member via a lumen of the medical of the medical device.

30. A system as claimed in claim 29 wherein the interface comprises a ramp feature.

31. A system as claimed in claim 29 wherein the interface comprises a portion of a funnel.

32. A system as claimed in claim 1 wherein the cross sectional area of the inner solid rod member added to the cross sectional area of the guidewire comprise substantially the cross sectional area of the tubular shaft lumen of the elongated tubular shaft.

33. A system as claimed in claim 1 wherein a marker band is provided at the distal end of the inner solid rod member.

34. A system as claimed in claim 33 wherein the marker band is attached to the inner solid rod member.

35. A system as claimed in claim 33 wherein the marker band is solid in construction.

36. A system as claimed in claim 1 wherein the inner solid rod member is rotationally fixed relative to the elongate shaft.

37. A system as claimed in claim 36 wherein the system comprises a key to prevent rotational movement.

38. A system as claimed in claim 37 wherein the key is provided in a portion of the elongate tubular shaft.

39. A system as claimed in claim 37 wherein the key is provided at the proximal guidewire port.

40. A system as claimed in claim 39 wherein a ramp is provided at the proximal guidewire port and the ramp defines the key.

41. A system as claimed in claim 37 wherein the key is provided in a handle portion of the catheter.

42. A system as claimed in claim 1 wherein the proximal guidewire port comprises an opening in the wall of the elongate shaft.

43. A system as claimed in claim 42 comprising a ramp for guiding the guidewire to the proximal guidewire port.

44. A system as claimed in claim 43 wherein the ramp comprises a tongue-like segment extending inwardly from the proximal guidewire port.

45. A system as claimed in claim 44 wherein the tongue extends into the surface pathway in the inner solid rod member.

46. A system as claimed in claim 45 wherein the tongue substantially fills the cross section of the surface pathway.

47. A system as claimed in claim 42 wherein the ramp surface has a cylindrical aspect.

48. A system as claimed in claim 24 wherein the tip is offset relative to the guidewire.

49. A system as claimed in claim 1 wherein the proximal guidewire port is sized so as to provide clearance to the guidewire.

50. A system as claimed in claim 1 wherein the proximal guidewire port is generally angulated in the direction of guidewire movement.

51. A system as claimed in claim 1 wherein the catheter is a filter delivery catheter.

52. A system as claimed in claim 51 wherein the elongate tubular shaft has a distal pod defining a reception space for a filter.

53. A system as claimed in claim 1 wherein the catheter is a stent delivery catheter.

54. A system as claimed in claim 53 wherein the elongate tubular shaft has a reception space at the distal end for reception of a stent.

55. A system as claimed in claim 53 wherein the inner solid rod member extends through a lumen defined by the stent.

56. A system as claimed in claim 55 wherein the inner solid rod member terminates in a distal tip.

57. A system as claimed in claim 1 wherein the catheter is a filter retrieval catheter.

58. A system as claimed in claim 57 wherein the elongate tubular shaft has a distal reception space for reception of a retrieved filter.

59. A system as claimed in claim 58 wherein the inner solid rod member extends through the reception space during positioning of the catheter for filter retrieval.

60. A system as claimed in claim 58 wherein the inner solid rod member projects distally of the distal end of the catheter to provide centering.

* * * * *